US008182832B2

(12) United States Patent
Berger et al.

(10) Patent No.: US 8,182,832 B2
(45) Date of Patent: *May 22, 2012

(54) BONE REPLACEMENT MATERIAL COMPRISING CRYSTALLINE PHASES

(75) Inventors: Georg Berger, Zepernick (DE); Andrea Spitzer, Berlin (DE); Christian Jäger, Berlin (DE); Jutta Pauli, Berlin (DE); Renate Gildenhaar, Berlin (DE)

(73) Assignee: Bam Bundesanstalt fur Materialforschung und-Prufung, Berlin (DE)

( * ) Notice: Subject to any disclaimer, the term of this patent is extended or adjusted under 35 U.S.C. 154(b) by 471 days.

This patent is subject to a terminal disclaimer.

(21) Appl. No.: 12/424,353

(22) Filed: Apr. 15, 2009

(65) Prior Publication Data
US 2009/0197972 A1 Aug. 6, 2009

Related U.S. Application Data

(63) Continuation of application No. 10/689,219, filed on Oct. 20, 2003, now Pat. No. 7,547,448.

(30) Foreign Application Priority Data
Oct. 21, 2002 (DE) ................................ 102 49 627

(51) Int. Cl.
A61F 2/28 (2006.01)
(52) U.S. Cl. ...................................................... 424/426
(58) Field of Classification Search .......................... None
See application file for complete search history.

(56) References Cited

U.S. PATENT DOCUMENTS
3,922,155 A 11/1975 Broemer et al.
(Continued)

FOREIGN PATENT DOCUMENTS
DE 197 44 809 C1 7/1999
(Continued)

OTHER PUBLICATIONS

Knabe, C. et al. (1997) "Morphological evaluation of osteoblasts cultured on different calcium phosphate ceramics," Biomaterials. 18: 1339-1347.

Primary Examiner — Carlos Azpuru
(74) Attorney, Agent, or Firm — Novak Druce + Quigg LLP

(57) ABSTRACT

The present invention relates to an X-ray amorphous-crystalline material with high solubility which can be used as a bioactive bone replacement material and as a substrate material in biotechnology. The new material comprising crystalline and X-ray amorphous phases is characterized in that according to $^{31}$P-NMR measurements, it contains $Q_0$-groups of orthophosphate and $Q_1$-groups of diphosphate, the orthophosphates or $Q_0$-groups making up 70 to 99.9% by weight relative to the total phosphorus content of the finished material and the diphosphates or $Q_1$-groups making up 0.1 to 30% by weight relative to the total phosphorus content of the finished material, and that according to X-ray diffractometric measurements and relative to the total weight of the finished material, 30 to 99.9% by weight of a main crystal phase consisting of $Ca_2K_{1-x}Na_{1+x}(PO_4)_2$, where x=0.1 to 0.9, is contained in the bone replacement material and 0.1 to 20% by weight of a substance selected from the group consisting of $Na_2CaP_2O_7$, $K_2CaP_2O_7$, $Ca_2P_2O_7$ and mixtures thereof is contained as a secondary crystal phase, the X-ray amorphous phases contained besides the main crystal phase jointly making up 0.1 to 70% by weight relative to the total weight of the finished material.

20 Claims, 1 Drawing Sheet $^{31}$P-MAS-Spectra of GA1 through GA3

U.S. PATENT DOCUMENTS 6,117,456 A 9/2000 Lee et al.
7,223,420 B2 5/2007 Berger et al.

FOREIGN PATENT DOCUMENTS

EP 0 237 043 B1 9/1987
WO 91/07357 A1 5/1991
WO WO 91/07357 * 5/1991

* cited by examiner

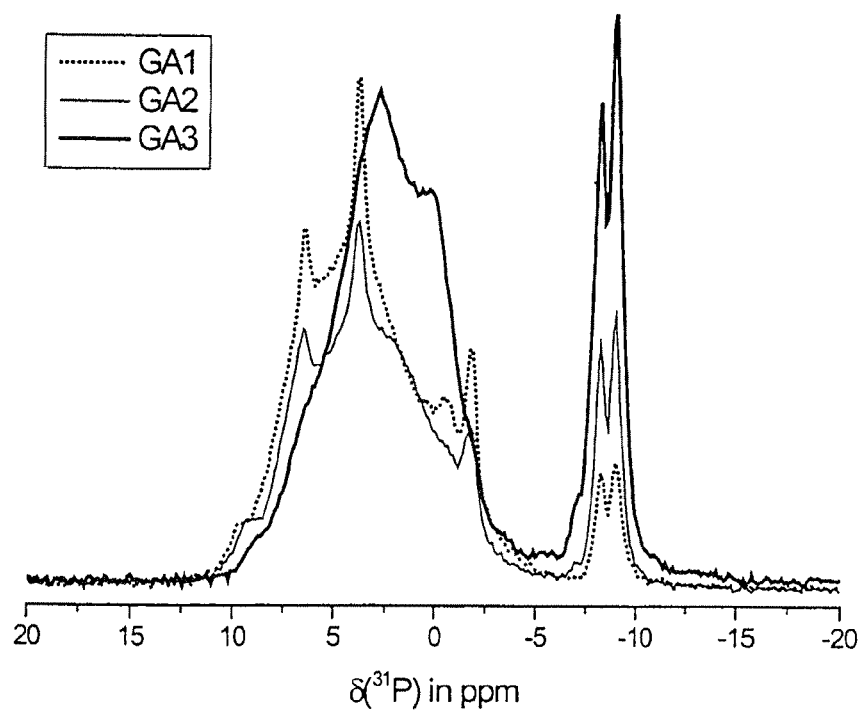
Fig. 1: $^{31}$P-MAS-Spectra of GA1 through GA3
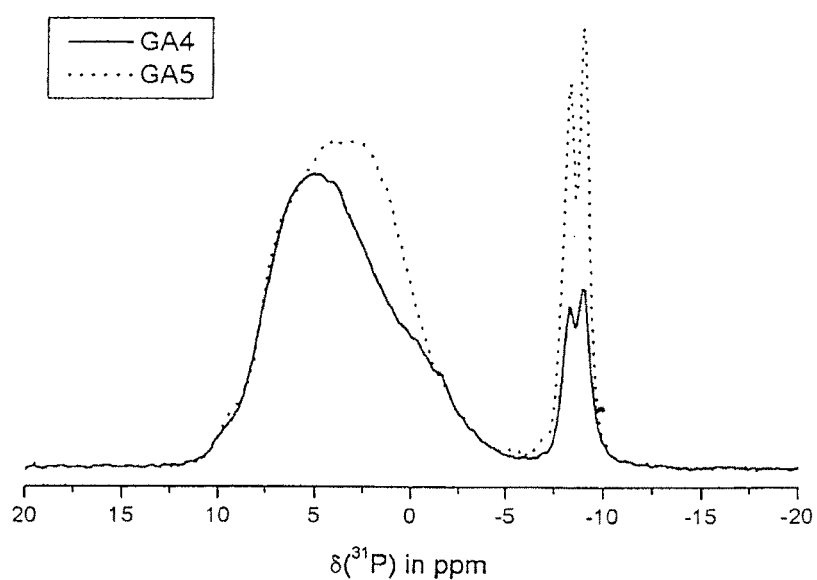
Fig. 2: $^{31}$P-MAS-NMR-Spectra of GA4 and GA5003055

BONE REPLACEMENT MATERIAL COMPRISING CRYSTALLINE PHASES

CROSS-REFERENCE TO RELATED APPLICATIONS

The present application is a continuation of prior application Ser. No. 10/689,219, filed Oct. 20, 2003, which claims priority to German Appln. 10249627.7 filed Oct. 21, 2002. This present application claims the benefit of the foregoing applications which are incorporated herein by reference in their entirety.

BACKGROUND OF THE INVENTION

1. Field of the Invention

The present invention relates to an X-ray amorphous-crystalline material with high solubility which can be used both as a bioactive bone replacement material, e.g. in the form of a coating applied onto metallic prosthesis sticks by thermal spraying or by rf sputtering, and as a substrate material in biotechnology, especially in tissue engineering, e.g. in the form of a ceramic sheet or of a compact or porous, i.e. spongiosa-like, scaffold-like, moulded body. The invention also relates to a manufacturing method.

2. Description of the Related Art

In principle, inorganic materials which are easily resorbed are known. Materials which are specifically used as bioactive bone replacement materials and dissolve quickly have also been described in the relevant literature. For example, there have been numerous publications dedicated to the successful clinical use of ceramic materials the main crystal phases of which are alpha- or beta-tricalcium phosphate (TCP). In addition, there have been comparative analyses of these two TCP phases using animal tests. It is known from EP 237043 that granulated materials made of alpha-TCP contain dicalcium phosphate on their surface, whose solubility was higher than that of the pure alpha-PCT core material, especially in the initial phase following an implantation.

The chemical solubility of the aforesaid granulated materials was surpassed by other bioactive materials based on calcium phosphates which in addition contain oxides of potassium, sodium, magnesium and/or silicon (EP 541564 B1) and the glassy-crystalline material of which is based on the following main crystal phases: Phase X, rhenanite, phase according to Ando (Phase A) and/or mixed crystals derived from the aforesaid phases.

SUMMARY OF THE INVENTION

The object of the invention is to provide an X-ray amorphous-crystalline material which enables a substantially direct joining of bones without connective tissue and/or the ex vivo cultivation of bone cells, and, which dissolves in contact with bone tissue, and which at the same time has high solubilities which are adjustable in a more precise manner and, in the case of composite materials, coefficients of expansion adapted to certain steels. Another object of the invention is to develop a method for manufacturing the aforesaid material as well as manufacturing aids.

According to the invention, the bone replacement material consists of crystalline and X-ray amorphous phases and contains:

according to $^{31}$P-NMR measurements, $Q_0$-groups of orthophosphate and $Q_1$-groups of diphosphate, the orthophosphates or $Q_0$-groups making up 70 to 99.9% by weight relative to the total phosphorus content of the finished material and the diphosphates or $O_1$-groups making up 0.1 to 30% by weight relative to the total phosphorus content of the finished material, and wherein according to X-ray diffractometric measurements and relative to the total weight of the finished material, 30 to 99.9% by weight of a main crystal phase consisting of $Ca_2K_{1-x}Na_{1+x}(PO_4)_2$, where x=0.1 to 0.9, is contained and 0.1 to 20% by weight of a substance selected from the group consisting of $Na_2CaP_2O_7$, $K_2CaP_2O_7$, $Ca_2P_2O_7$ and mixtures thereof is contained as a secondary crystal phase, and wherein the X-ray amorphous phases contained besides the main crystal phase jointly make up 0.1 to 70% by weight relative to the total weight of the finished material.

The secondary crystal phase is preferably made up of diphosphates, but one or more of the substances $NaPO_3$, $KPO_3$ and mixtures thereof can also be contained, the chain phosphates $NaPO_3$ and $KPO_3$ being detectable as $Q_2$-groups according to $^{31}$P-NMR measurements. The chain phosphates are contained in an amount ranging between 0.1 and 10% by weight, preferably 0.1 and 4% by weight.

Further, the secondary phase may contain a silicate phase in an amount ranging up to 6% by weight, corresponding to the $SiO_2$ content.

The aforesaid main crystal phase and the constituents of the secondary crystal phase may contain magnesium in an amount ranging up to 10% by weight, calculated as MgO and relative to the weight of the finished material.

The orthophosphate phase represented by $Q_0$-groups preferably makes up 75 to 99% by weight, particularly 78 to 95% by weight.

The diphosphate phase represented by $Q_1$-groups preferably makes up 1 to 22% by weight, particularly 5 to 16% by weight.

The composition of the X-ray amorphous-crystalline material with high solubility which is based on CaO, $P_2O_5$, $Na_2O$, $K_2O$, MgO and optionally $SiO_2$ ranges between (in % by weight):

| | | | |
|---|---|---|---|
| 30 and 55 | $P_2O_5$; | 5 and 50 | CaO; |
| 1 and 20 | $Na_2O$; | 0.5 and 20 | $K_2O$; |
| 0 and 13 | MgO; | 0 and 10 | $SiO_2$; |

MgO or $SiO_2$ or a mixture thereof making up at least 1% by weight.

A preferred X-ray amorphous-crystalline material is composed as follows (in % by weight): 35 to 48 $P_2O_5$, 28 to 38 CaO, 2.5 to 15 $Na_2O$, 1.5 to 18 $K_2O$, 0.1 to 4 MgO, 0.0 to 3 $SiO_2$. A special preferred embodiment contains 40 to 52 $P_2O_5$, 28 to 33 CaO, 8.5 to 13 $Na_2O$, 9.5 to 15 $K_2O$, 1.5 to 3 MgO, 0.1 to 4 $SiO_2$.

In general, the term "X-ray amorphous-crystalline" material used herein cannot be clearly defined. "X-ray amorphous" as used herein refers to a material whose structure cannot be determined using standard XRD (X-ray diffractometry). The undetectable areas can be very small organized areas (micro-crystalline) as well as statistically unorganized areas. Unlike XRD, the $^{31}$P-NMR results can be used to detect the existence of any crystalline phase. Therefore quantitative estimates based on NMR and XRD results can be rather different. In the present case, this phenomenon seems to be particularly true of the diphosphate and chain phosphate contents; as a rule, $^{31}$P-NMR measurements yield considerably higher contents than XRD. In some cases, no contents at all are found using XRD. This impressively shows why $^{31}$P-NMR measurements are an essential prerequisite for characterizing and finally manufacturing the materials according to the invention. XRD measuring was made with PW 1710, Philipps, NL (CuK radiation).

Both crystalline and X-ray amorphous phases can therefore be provided in a thoroughly mixed state. It is of no importance for the present invention whether one phase is located adjacent to the other or one phase encloses the other. The term "main crystal phase" as used herein refers to a crystalline phase which is detected using X-ray diffraction and is contained in at least twice the amount of a secondary phase, concentrations of 20% and below, preferably below 15% by weight, being referred to as secondary phases.

For the sake of clarity, it must be pointed out that "$Ca_2KNa(PO_4)_2$" can certainly be identified as main crystal phase. However, there are shifts of intensity in the individual compositions, which may be rather substantial in some cases, due to the varying ratio of sodium to potassium or the inclusion of other ions (e.g. $Mg^{2+}$ or $SiO_4^{4-}$) so that the formula "$Ca_2K_{1-x}Na_{1+x}(PO_4)_2$, where x=0.1-0.9" is to be used. Higher Na contents are preferred, e.g. x=0.2-0.9.

Surprisingly, solubility has been found to be particularly high if the product obtained by the melting process contains in particular crystalline diphosphates such as $Na_2CaP_2O_7$, $K_2CaP_2O_7$ and/or $Ca_2P_2O_7$ or even a majority of X-ray amorphous diphosphates besides the main crystal phases and X-ray amorphous orthophosphates. Further, it was surprisingly found that the aforesaid statement can be clearly quantified using $^{31}P$-NMR measurements.

The $^{31}P$-NMR measurements, which were carried out using a superconductive Fourier NMR spectrometer known as Avance DMX40 WB and manufactured by Bruker BioSpin GmbH (Germany), showed that the material consists of 70 to 99.9% by weight orthophosphate of calcium and in some cases orthophosphate of sodium, potassium and magnesium, wherein the aforesaid orthophosphate content is determined using $^{31}P$-NMR measurements of $O_0$-groups and refers to crystalline and/or X-ray amorphous material in its entirety. In addition, 0.1 to 30% by weight diphosphate of calcium and in some cases diphosphate of sodium, potassium and magnesium was found, wherein the aforesaid diphosphate content can be reliably determined using $^{31}P$-NMR measurements ($Q_1$-groups) and refers to crystalline and/or X-ray amorphous material in its entirety.

Further, it is advantageous that 0.1 to 10% by weight chain phosphate consisting of sodium phosphate or potassium phosphate or both be contained, wherein this chain phosphate content represented by $Q_2$-groups is reliably determined by means of $^{31}P$-NMR measurements and refers in particular to amorphous and, as the case may be, crystalline material in its entirety. In addition, 0.1 to 10% by weight of a silicate phase may be contained, depending upon the amount of $SiO_2$ added. Moreover, $Ca_5Na_2(PO_4)_4$ may be contained, although this is not preferred.

Further, it has surprisingly been found that the desired effect, i.e. a considerably improved solubility, is brought about by the presence of diphosphates and/or chain phosphates, preferably diphosphates, as will be demonstrated in Example 3.

The diphosphate contents result from a comparatively high phosphate content relative to the other constituents. The aforesaid phosphate content could also be the reason why the compositions according to the invention melt very easily yielding a rather fluid melt compared to known resorbable materials. Such a low-viscosity melt has the advantage that it has a better processability. That is the case for a frit of the melt or a direct blowing of the melt etc.

Further, it has surprisingly been found that due to the presence of diphosphates the ion discharge behaviour of the material (the X-ray amorphous-crystalline material), which in the beginning shows a strong alkaline reaction, changes more pronouncedly towards physiological pH values (7.4) than that of materials not containing diphosphate, provided the material was stored in deionized water. Due to this shift in pH values, the material is also of interest to biotechnology, in particular to tissue engineering.

The aforesaid feature can be enhanced by boiling a (compact or open-pore) moulded body in deionized water (37-90° C.) thus leaching its surface so that the material or moulded body treated in this way has considerably lower pH values once the treatment is finished. This phenomenon could be put down to a reduction of the alkaline cations in the area near the surface of the material. The aforesaid process can be accelerated by boiling the material in a reactor, advantageously at a pressure of up to 10 bars. Such an embodiment of the invention is preferred.

It is an advantageous feature of the material according to the invention that its solubility can be adjusted within relatively wide ranges, depending upon the selected composition; specifically, the total solubility can range between 30 and 500 µg/mg relative to the starting material if the test is carried out in 0.2M TRIS-HCl buffer solution at pH=7.4, T=37° C. using a grain size fraction of 315-400 µm, the duration of the test being 120 h and the ratio of weighed-in sample to buffer solution being 50 mg to 40 ml.

The material according to the invention is manufactured by combining the substances suitable for preparing the mixture to be melted, their concentrations (relative to the total weight of the material) being in the range of 30-55% by weight CaO, 35-50% by weight $P_2O_5$, 1-20% by weight $Na_2O$, 0.5-20% by weight $K_2O$ and 0.1-5% by weight MgO and optionally up to 5% by weight $SiO_2$, and melting them at between 1,550 and 1,650° C. in a suitable crucible material, e.g. consisting of a Pt/Rh alloy, using multistage thermal treatment programmes including holding stages in the range between 200 and 1,500° C., namely 1-2 h at 350-400° C., 750-850° C. and 950-1,050° C., e.g. 1 h at 400, 800 and 1,000° C. respectively. The melt is poured, preferably following a holding time of between 10 and 60 min, and once the mass has solidified it is cooled down to room temperature in air (spontaneous cooling) or in a cooling furnace using a temperature-controlled cooling process, e.g. at a rate of 1 to 20 degrees/min, depending upon its intended use. The melt can also be blown thus directly forming the melt into spherical granules. In both cases, a spontaneous crystallization process takes place while the melt cools down. The mixture to be melted may comprise oxides, carbonates, hydrogen phosphates and/or ortho-phosphoric acid. The $^{31}P$-NMR measurements yield different spectra allowing conclusions as to the raw materials used or indicating small amounts of iron oxides or manganese oxides contained therein. Preferred melting temperatures range between 1,590 and 1,650° C.

Once the material has cooled down, it is granulated and used as a bone replacement material, but it can e.g. also be ground, mixed with commonly used sintering aids and be isostatically pressed into moulded bodies in order to obtain a densely fired ceramic body after sintering. In general, the sintering temperatures range between 900 and 1,200° C.

Alternatively, the material manufactured according to the invention can e.g. be ground, mixed with commonly used sintering aids and processed into a slurry which is then applied onto a polyurethane sponge and sintered in several sintering stages at such high temperatures that the polyurethane sponge and the sintering aids are burnt completely and a spongiosa-like body is obtained the main crystalline constituents of which are $Ca_2K_{1-x}Na_{x+1}(PO_4)_2$ (x=0.1-0.9) and $Na_2CaP_2O_7$, $K_2CaP_2O_7$, $Ca_2P_2O_7$ and/or mixed crystals in between these phases.

In a preferred embodiment of the invention, some of the raw materials used are melted separately in order to obtain a glass which acts as a sintering aid and can be used for the production of the spongiosa-like bodies in a particularly advantageous manner. The aforesaid glass is ground and can be added to the slurry consisting of the material according to the invention which has been ground following the melting and cooling processes and then processed into a slurry. The glass melted separately can be added to the slurry in an amount ranging between 0.5 and 15, preferably 4-8% by weight, relative to the amount of solid matter contained therein, providing, however, that the individual components are not contained in the composition in larger amounts than those indicated in the invention. Such a glass can in particular be produced on the basis of $SiO_2$, MgO and $Na_2O$.

In this embodiment, the sintering process leads to a very solid structure of the moulded body, whereas parts of the moulded body may crumble away if all components are melted together and then sintered. The glass melted separately has a grain size $D_{50}$ ranging between 0.7 and 7 μm when being added to the ground material, whose grain size is similar or larger.

Therefore the present invention also relates to a glass used as a sintering aid for resorbable materials containing calcium phosphates with the exception of tri-calcium phosphate, which glass is characterized by the following chemical composition in % by weight:

| | |
|---|---|
| $SiO_2$: | 68-78, preferably 73-78, particularly 74-75 |
| MgO: | 5-12, preferably 8-11, particularly 8.5-10 |
| $Na_2O$: | 12-27, preferably 12-19, particularly 14.5-17 |
| $K_2O$: | 0-22, preferably 0-5 |
| $P_2O_5$: | 0-20, preferably 0-10. |

Another processing option consists in grinding the material, adding commonly used sintering aids and processing the slurry obtained in this way into a sheet which has an open-pore structure once the firing process is finished.

Advantageously, the material according to the invention can also be provided in combination with a metallic implant surface. The material's coefficient of expansion ranges between 12 and $18 \times 10^{-6}$ $K^{-1}$, measured using a dilatometer (silica glass pushrod dilatometer (Kieselglas-Schubstangen-Dilatometer) manufactured by Netzsch Gerätebau GmbH, Germany), so that an adaptation to known steels, e.g. chromium-cobalt-molybdenum steels having similar coefficients of expansion, is particular advantageous.

The present invention also relates to the use of the X-ray amorphous-crystalline material according to the invention for manufacturing granulated materials, ceramic bodies or ceramic sheets.

The invention will hereinafter be explained by means of examples. All percentages are by weight unless indicated otherwise.

BRIEF DESCRIPTION OF THE DRAWINGS

FIG. 1: shows $^{31}$P-MAS-NMR spectra of the materials GA 1, GA 2 and GA 3 according to the invention, whose composition corresponds to Example 1 and whose phases correspond to Example 5 (MAS=Magic Angle Spinning);

FIG. 2: shows the $^{31}$P-MAS-NMR spectra of the materials GA 4 and GA 5 according to the invention, whose composition corresponds to Example 2 and whose phases correspond to Example 5.

DETAILED DESCRIPTION OF THE INVENTION

Example 1

The following materials were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| GA 1 | 30.67 | 2.45 | 43.14 | 9.42 | 14.32 | 0.00 |
| GA 2 | 29.92 | 2.39 | 44.53 | 9.19 | 13.97 | 0.00 |
| GA 3 | 29.21 | 2.33 | 45.85 | 8.97 | 13.64 | 0.00 |

To facilitate understanding, this melting process can also be described as follows: GA 1; GA 2 (=GA 1+2.5% $P_2O_5$); GA 3 (=GA 1+5% $P_2O_5$).

The mixtures to be melted were weighed in as follows:

| Code | $CaCO_3$ In g | MgO in g | 85% $H_3PO_4$ in ml | $Na_2CO_3$ in g | $K_2CO_3$ in g | $SiO_2$ in g |
|---|---|---|---|---|---|---|
| GA 1 | 54.4 | 2.45 | 41.48 | 16.11 | 21.01 | 0 |
| GA 2 | 53.40 | 2.39 | 42.82 | 15.72 | 20.50 | 0 |
| GA 3 | 52.13 | 2.33 | 44.09 | 15.34 | 20.01 | 0 |

First, the components comprising calcium, magnesium, sodium and potassium and optionally silicon, are weighed in. Once the weighing-in process is finished, each mixture is mixed in a tumbling mixer for one hour. Then the 85% orthophosphoric acid is added to the mixture, the mixture is thoroughly ground in a mortar, stirred and dried at 100° C. for one hour, ground in a mortar again and stored once more in a drying chamber at 100° C. for one hour. Subsequently, the mixture was once again ground in a mortar, filled into a Pt/Rh crucible and heated up to 400° C., at which temperature it was held for one hour, then heated up to 800° C., at which temperature it was again held for one hour, and then heated up to 1,000° C., at which temperature it was also held for one hour. The sinter cake produced in this way was cooled in air and ground in a mortar again in order to make it more homogeneous. The pretreated mixture was then filled into a platinum crucible and heated up to 1,600° C. in a melting furnace. Once the aforesaid temperature had been reached, the melt was maintained at this temperature for half an hour. The low-viscosity, homogeneous melts were then poured onto a steel plate and pressed using a second steel plate so that a salt-like solidified plate was obtained. The crystallization taking place during this stage gives an opaque, white colour to the bodies obtained by the melting process.

Example 2

Following the same production procedure as described in Example 1, i.e. preparing a mixture of calcium carbonate, sodium carbonate, potassium carbonate and orthophosphoric acid, the following compositions were synthesized according to the amounts indicated in the table in % by weight:

| Code | CaO | MgO | P$_2$O$_5$ | Na$_2$O | K$_2$O | SiO$_2$ |
|---|---|---|---|---|---|---|
| GA 4 | 31.54 | 1.19 | 42.37 | 9.17 | 13.95 | 1.78 |
| GA 5 | 30.79 | 1.16 | 43.74 | 8.95 | 13.62 | 1.73 |

Low-viscosity melts were obtained for all compositions, which melts spontaneously crystallized when being cooled. The crystallization products had a white colour.

Example 3

Another manufacturing option consists, inter alia, in that the amount of phosphorus or phosphate may be brought in by means of a calcium carrier, either in its entirety or, as in the present example, in part. The following composition was synthesized according to the amounts indicated in the table in % by weight:

| Code | CaO | MgO | P$_2$O$_5$ | Na$_2$O | K$_2$O | SiO$_2$ |
|---|---|---|---|---|---|---|
| GA 1 | 30.67 | 2.45 | 43.14 | 9.42 | 14.32 | 0.00 |

The mixture to be melted was weighed in as follows:

| Code | CaCO$_3$ in g | Magnesium hydroxide carbonate in g | 85% H$_3$PO$_4$ in ml | Na$_2$CO$_3$ in g | K$_2$CO$_3$ in g | CaHPO$_4$ in g |
|---|---|---|---|---|---|---|
| GA 1 | 0.00 | 5.13 | 4.25 | 16.11 | 21.00 | 74.43 |

The mixture to be melted was weighed in according to the amounts indicated above, mixed in a tumbling mixer for one hour, phosphoric acid was added, the mixture was dried at 100° C. for one hour, cooled in air and ground in a mortar. The mixture obtained in this way was filled into a platinum crucible, placed in a furnace which had been preheated to 450° C. and held at this temperature for 6 hours, and was then placed in a furnace which had been preheated to 800° C. and held at this temperature for 16 hours. The crucible was taken out and the furnace was preheated to 950° C. The crucible was then held in the furnace preheated to 950° C. for 6 hours. Subsequently, the sample was heated up to 1,600° C. and held at this temperature for half an hour. The low-viscosity, homogeneous melt was then poured onto a steel plate and pressed using a second steel plate so that a salt-like solidified plate was obtained. The crystallization taking place during this stage gives an opaque, white colour to the bodies obtained by the melting process. A discoloration can be observed, depending upon the CaHPO$_4$ component used and undesirable amounts of iron and/or manganese contained therein.

It is also possible to directly quench the melt in a water bath once the melting process (1,600° C., 0.5 h) is finished (fritting) in order to facilitate the further comminution of the product obtained by the melting process if it is to be further processed in the form of a slurry.

Example 4

The samples according to Example 1 and selected samples according to Example 2 (see the following table) were used to produce granulated materials having a grain size ranging between 315 μm and 400 μm in order to determine solubility. The solvent used was 0.2M TRIS-HCl buffer solution with a pH value of 7.4 and at a temperature of 37° C. The analyzed amount was 50 mg using 40 ml solvent. The granulated materials were stored at 37° C. for a period of 120 h. Subsequently, the total solubility was determined by determining the individual ions (of Ca, Mg, P, Na, K) in the solution by means of an ICP measurement:

| Code | Solubility [μg/mg] |
|---|---|
| GA 1 | 95 ± 8 |
| GA 2 | 134 ± 16 |
| GA 3 | 221 ± 22 |
| GA 4 | 90 ± 8 |
| GA 5 | 152 ± 10 |

Example 5

$^{31}$P-MAS-NMR spectra of the samples according to Example 1 and Example 2 were recorded with a waiting time of 120 s between the individual pulses. The samples rotated at a speed of 12.5 kHz.

The quantitative composition of the samples as regards their phosphate content is indicated in the following table:

| Code | Orthophosphate content [(PO$_4$)$^{3-}$] in % | Diphosphate content [(P$_2$O$_7$)$^{2-}$] in % | chain phosphate content [predominantly (PO$_3$)$^{1-}$] in % |
|---|---|---|---|
| GA 1 | 99.5-96 | 0.5-4 | — |
| GA 2 | 88 | 12 | — |
| GA 3 | 79 | 21 | — |
| GA 4 | 95 | 5 | — |
| GA 5 | 89 | 11 | — |

The range indicated for the composition GA 1 is based on the analysis of three batches one of which was synthesized according to the manufacturing method described in Example 3, whereas only one sample was analysed for each of the other compositions.

Example 6

In the zirconium oxide bowl (250 ml) of a planetary mill, the product obtained by the melting process having a composition according to code GA 1 was ground two times for 20 min. The result is shown in the following table.

| Code | D$_{50}$ value [in μm] |
|---|---|
| GA 1 | 6.50 |

Example 7

The ground GA 1 sample according to Example 6 is to be processed into "scaffolds". For this purpose, a slurry was produced by combining 100 g of the ground material with 45 g of a mixture consisting of 90% polyethylene glycol and 10% of a commercially available surface-active agent and adding 5 ml isopropyl alcohol. The slurry obtained in this way is applied onto open-pore PUR sponges (PUR=polyurethane) whose porosity ranges between 80 and 20 ppi (pores per inch) by repeatedly immersing and squeezing the sponges, dried overnight in a drying chamber at 120° C. and then slowly heated up to 1,000° C. at a rate of 10° C. per minute. The result is a spongiosa-like material the structure of which resembles that of the sponge used, while the PUR sponge has burnt completely.

Example 8

In order to further increase the strength of the spongiosa-like bodies, 3% by weight of a previously produced glass having a chemical composition of (in % by weight) 74.97 $SiO_2$, 9.22 MgO and 15.81 $Na_2O$ (melted as 27.04 $Na_2CO_3$) and a $D_{50}$ value of 6.56 μm was added to the ground material according to GA 1 as a sintering aid. Then a slurry was produced by combining 100 g of this powder mixture with 45 g of a mixture consisting of 90% polyethylene glycol and 10% of a commercially available surface-active agent and adding 5 ml isopropyl alcohol. The slurry obtained in this way is applied onto open-pore PUR sponges whose porosity ranges between 80 and 20 ppi (pores per inch) by repeatedly immersing and squeezing the sponges, dried overnight in a drying chamber at 120° C. and then slowly heated up to 1,000° C. at a rate of 10° C. per minute. The result is a spongiosa-like material the structure of which resembles that of the sponge used, while the PUR sponge has burnt completely.

Example 9

Samples according to Example 1 and Example 2 were produced and analyzed by means of $^{31}$P-NMR measurements. The $^{31}$P-MAS-NMR spectra were recorded with a waiting time of 120 s between the individual pulses. The samples rotated at a speed of 12.5 kHz.

As a result, it can be shown that in the case of the samples GA 1 through GA 3 (cf. FIG. 1), whose only chemical difference consists in the increasing phosphate content, this increased phosphate content is reflected in an X-ray amorphous-crystalline diphosphate content in the product obtained by the melting process, which also dramatically influenced solubility (cf. Example 4). This applies analogously to the samples GA 4 and GA 5 (cf. FIG. 2).

In the spectra shown in FIG. 1 and FIG. 2, the left (broader) peaks indicate the $Q_0$-groups and the right (narrower) peaks the $Q_1$-groups.

Example 10

Material composed according to code GA 1 was freshly ground, 1 g of a grain size fraction <45 μm was added into 100 ml E-pure water, and the pH value was determined after 1 min and after 72 h. The result was 10.55 after one minute and 8.71 after 72 hours, i.e. a clear change towards physiological conditions could be observed.

Example 11

In order to enhance this effect a priori, the following experiment was carried out: A spongiosa like body was produced according to Example 7, i.e. the composition according to code GA 1 was applied onto a PUR sponge and sintered, except that the sponge used in the present example had a porosity of 30 ppi.

The moulded body obtained in this way, whose outer dimensions were approx. 11 mm×11 mm×7 mm, was immersed in 100 ml E-pure water and the pH value was measured after 10 min. The measured value was 9.62.

Subsequently, the moulded body was eluted in E-pure water at 60° C. and a pressure of 3 bars for one hour. The moulded body was then rinsed 5 times in 20 ml fresh E-pure water, immersed in 100 ml E-pure water again, and a pH value of 8.83 was measured after 1 hour.

This demonstrates that the pretreatment of spongiosa-like bodies described above is a useful activity as products pretreated in this way have a lower basicity, which can be advantageous both for implantation in vivo and for tissue engineering ex vivo or in vitro.

Example 12

An important feature with regard to the coating of materials with the resorbable materials according to the invention consists in that the thermal coefficient of expansion can be varied, bearing in mind e.g. that this coefficient is approx. $8 \cdot 10^{-6}$ $K^{-1}$ for titanium implants and approx. $14\text{-}16 \cdot 10^{-6}$ $K^{-1}$ for Co—Cr—Mo steels (depending upon the constituents of the alloy). In order to obtain a composite material which is optimally suited to its intended use, the temperature range in which the material is applied onto the metallic substrate must be carefully selected as in this way the substrate can be subjected to compressive strain, i.e. to preheating, in a targeted manner during the coating process thus obtaining a composite material which in general is regarded as mechanically more stable.

The following table shows some of the possible variations:

| Sample | $CE_{30\text{-}100}$ ($10^{-6} K^{-1}$) | $CE_{RT**400}$ ($10^{-6} K^{-1}$) | $CE_{50\text{-}400}$ ($10^{-6} K^{-1}$) |
| --- | --- | --- | --- |
| GA 1 | 12.15 | 14.84 | 15.14 |
| GA 2 | 13.64 | 17.16 | 17.54 |
| GA 3 | 13.21 | 16.99 | 17.45 |
| GA 4 | 12.51 | 15.85 | 16.20 |
| GA 5 | 13.29 | 16.69 | 17.08 |

In the table, $CE_{30\text{-}100}$ is the coefficient of expansion between 30 and 100° C., $CE_{RT**400}$ is the coefficient of expansion between room temperature (25) and 400° C., and $AK_{50\text{-}400}$ is the coefficient of expansion between 50 and 400° C.

What is claimed is:

1. A bone replacement material comprising crystalline and X-ray amorphous phases, characterized in that
   a) according to $^{31}$P-NMR measurements, said bone replacement material comprises $Q_0$-groups of orthophosphate and $Q_1$-groups of diphosphate, the orthophosphates or $Q_0$ groups making up 70 to 99.9% by weight relative to the total phosphorus content of the finished material and the diphosphates or $Q_1$-groups making up 0.1 to 30% by weight relative to the total phosphorus content of the finished material, and
   b) according to X-ray diffractometric measurements and relative to the total weight of the finished material, 30 to 99.9% by weight of a main crystal phase consisting of $Ca_2K_{1-x}Na_{1+x}(PO_4)_2$ where x=0.1 to 0.9, is contained in the bone replacement material and 0.1 to 20% by weight of a substance selected from the group consisting of $Na_2CaP_2O_7$, $K_2CaP_2O_7$, $Ca_2P_2O_7$ and mixtures thereof is contained as a secondary crystal phase.

2. A bone replacement material according to claim 1, wherein additionally one or more of the chain phosphates $NaPO_3$, $KPO_3$ and mixtures thereof are contained in an amount ranging between 0.1 and 10% by weight, which chain phosphates can be detected as $Q_2$-groups using $^{31}$P-NMR measurements.

3. A bone replacement material according to claim 1, wherein in the processed, finished state said material consists of (in % by weight): 30 to 55% $P_2O_5$, 25 to 50% CaO, 1 to 20% $Na_2O$, 0.5 to 20% $K_2O$, 0 to 13% MgO, 0 to 10% $SiO_2$; and MgO or $SiO_2$ or a mixture thereof making up at least 1% by weight.

4. A bone replacement material according to claim 3, wherein MgO is in the range of 1-13% by weight and $SiO_2$ is in the range of 0.5-5% by weight; and MgO or $SiO_2$ or a mixture thereof making up at least 1% by weight.

5. A bone replacement material according to claim 4, wherein said material contains 40 to 52% $P_2O_5$; 28 to 33% CaO; 8.5 to 13% $Na_2O$; 9.5 to 15% $K_2O$; 1.5 to 3% MgO; and 0.1 to 4% $SiO_2$.

6. A bone replacement material according to claim 1, wherein x ranges between 0.2 and 0.9.

7. A bone replacement material according to claim 1, wherein the secondary crystal phase contains 0.1-4 wt-% of a silicate phase.

8. A bone replacement material according to claim 1, further comprising magnesium in an amount ranging up to 10% by weight, calculated as MgO and relative to the weight of the finished material, is contained.

9. A bone replacement material according to claim 1, wherein the orthophosphate phase represented by $Q_0$-groups makes up 75 to 99% by weight.

10. A bone replacement material according to claim 9, wherein the orthophosphate phase represented by $Q_0$-groups makes up 78 to 95% by weight.

11. A bone replacement material according to claim 1, wherein the diphosphate phase represented by $Q_1$-groups makes up 1 to 22% by weight.

12. A bone replacement material according to claim 11, wherein the diphosphate phase represented by $Q_1$-groups makes up 5 to 16% by weight.

13. A bone replacement material according to claim 1, wherein the secondary crystal phase makes up 0.1 to 15% by weight.

14. A bone replacement material according to claim 13, wherein the secondary crystal phase makes up 1 to 15% by weight.

15. A bone replacement material according to claim 1, wherein the total solubility ranges between 30 and 500 µg/mg, relative to the starting material if the test is carried out in 0.2M TRIS-HCl buffer solution at pH=7.4, T=37° C. using a grain size fraction of 315-400 µm, the duration of the test being 120 h and the ratio of weighed-in sample to buffer solution being 50 mg to 40 ml.

16. A bone replacement material according to claim 1, wherein the coefficient of expansion ranges between 12 and $18 \times 10^{-6}$ $K^{-1}$, measured using a dilatometer.

17. A bone replacement material according to claim 1, wherein the pH value of the surface changes by at least 0.7 units, preferably at least 1.5 units, towards the neutral point within the alkaline range if the material is stored in deionized water at room temperature for 72 hours or heated up to 60° C. for 1 hour at a pressure of 1-3 bars and rinsed with deionized water.

18. A bone replacement material according to claim 1, wherein said material is provided in combination with a metallic implant surface.

19. A bone replacement material according to claim 1, wherein said material is provided in the form of granulated materials, ceramic bodies or ceramic sheets.

20. The bone replacement material according to claim 1, wherein the X-ray amorphous phases contained besides the main crystal phase jointly make up 0.1 to 70% by weight relative to the total weight of the finished material.

* * * * *